United States Patent [19]

Beylin et al.

[11] Patent Number: 4,806,654

[45] Date of Patent: Feb. 21, 1989

[54] PROCESSES FOR THE PREPARATION OF BENZO(CHALCOGENO)(4,3,2-CD)INDAZOLES AND INTERMEDIATES THEREOF

[75] Inventors: Vladimir G. Beylin; Om P. Goel; Anthony D. Sercel; Howard D. H. Showalter, all of Ann Arbor, Mich.

[73] Assignee: Warner-Lambert Company, Morris Plains, N.J.

[21] Appl. No.: 149,103

[22] Filed: Feb. 11, 1988

Related U.S. Application Data

[63] Continuation-in-part of Ser. No. 29,021, Mar. 23, 1987, abandoned.

[51] Int. Cl.$^4$ .................. C07D 491/06; C07D 495/06
[52] U.S. Cl. .................................................. 548/370
[58] Field of Search ......................................... 548/370

[56]  References Cited

U.S. PATENT DOCUMENTS 4,604,390  8/1986  Elslager et al. ..................... 548/370

*Primary Examiner*—Robert W. Ramsuer
*Attorney, Agent, or Firm*—Elizabeth M. Anderson

[57] ABSTRACT

Improved processes for producing substituted benzo(-chalcogeno)[4,3,2-cd] indazoles. The processes produce compounds in higher yields and of greater purity by using a novel sequence of acylation chemistry and easily removed protecting groups. The compounds produced have antibacterial, antifungal, antileukemic, and antitumor activity.

21 Claims, No Drawings

PROCESSES FOR THE PREPARATION OF BENZO(CHALCOGENO)(4,3,2-CD)INDAZOLES AND INTERMEDIATES THEREOF

This is a continuation-in-part of U.S. Application Ser. No. 029,021 filed Mar. 23, 1987 now abandoned.

BACKGROUND OF THE INVENTION

The compounds of the present invention have been described in U.S. Pat. No. 4,604,390 herein incorporated by reference. Processes for preparing the compounds are also described therein.

The compounds are useful as antibacterial and antifungal agents. The compounds have also antineoplastic activity as demonstrated by in vitro and in vivo activity against leukemia.

SUMMARY

The present invention relates to improved processes for the preparation of substituted benzo(chalcogeno)[4,3,2-cd]indazoles. The present invention is better suited for large scale production, has greater yields, a more pure product, and provides for easier removal of the protecting group. The chalcogens of the present application include the elements oxygen, sulfur, and selenium.

One synthesis is for compounds having the formula

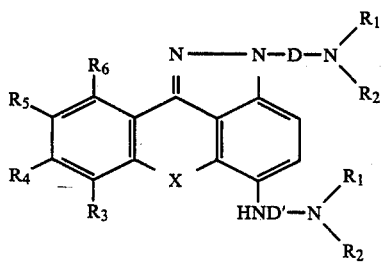

wherein
X is oxygen, sulfur, or selenium;
D and D' may be the same or different and are a straight or branched alkylene group of from two to five carbon atoms;
$R_1$ and $R_2$ may be the same or different and are hydrogen or an alkyl group of from two to eight carbon atoms which may be substituted by hydroxy;
$R_3$, $R_4$, $R_5$, and $R_6$ may be the same or different and are hydrogen or hydroxy; or a pharmaceutically acceptable salt thereof. The process proceeds as follows. Compounds of formula

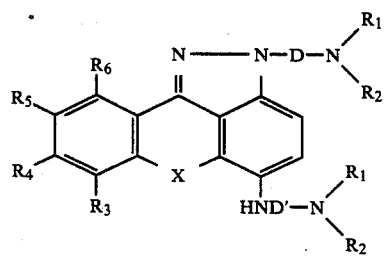

wherein $R_1$, $R_2$, $R_3$, $R_4$, $R_5$, $R_6$, D, D' and X are as described above and produced by (a) reacting an alkoxy-substituted compound of the formula

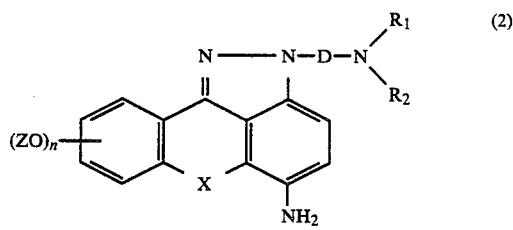

wherein Z is an alkyl of from one to four carbon atoms, n is an integer from one to four, and $R_1$, $R_2$, X and D are as described above, with boron tribromide in a suitable organic solvent then methanol to break up the boron complex to give a hydroxylated compound of the formula

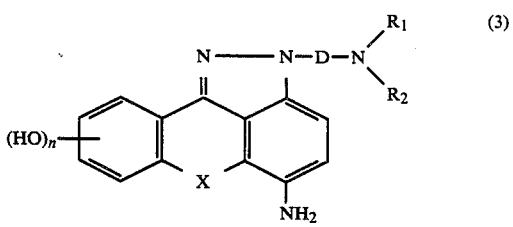

wherein X, D, $R_1$, $R_2$, and n are as described above, (b) reacting a compound of Formula 3 with the N-acylimidazole derived from reaction of 1,1'-carbonyldiimidazole and [(1,1-dimethylethoxy)carbonyl]amino acid to give the BOC-protected amino acid compound of formula

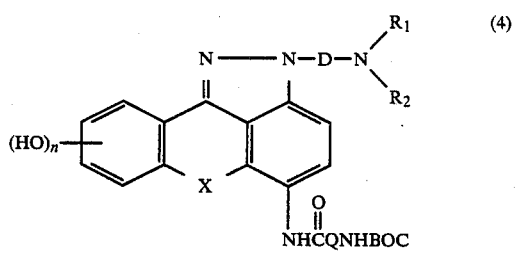

wherein X, $R_1$, $R_2$, D, and n are as described above, and Q is a straight or branched alkylene group of from one to four carbon atoms, (c) reducing the carbonyl portion of a compound of Formula 4 to the corresponding methylene containing Compound 5,

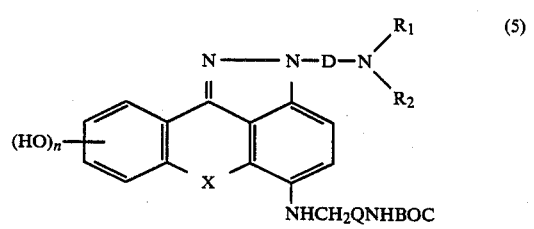

(d) isolating Compound 5 by flash chromatography,
(e) removing the BOC-protecting group from 5 by reaction with acid to produce a compound of the instant invention of Formula 1 above.

Another synthesis for compounds of Formula 1 which provides a very highly pure product is a process for the preparation of a substituted benzo(chalcogeno)[4,3,2-cd]indazole of the formula

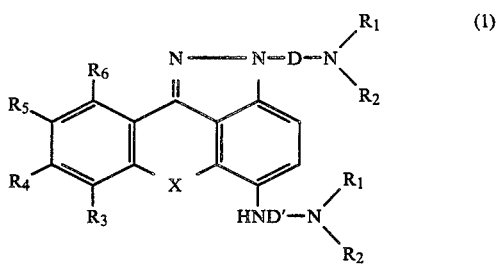

or a pharmaceutically acceptable salt thereof, wherein X is oxygen, sulfur, or selenium;

D and D' may be the same or different and are a straight or branched alkylene group of from two to five carbon atoms;

$R_1$ and $R_2$ may be the same or different and are hydrogen or an alkyl group of form two to eight carbon atoms which may be substituted by hydroxy; and $R_3$, $R_4$, $R_5$, and $R_6$ may be the same or different and are hydrogen or hydroxy which comprises:

(a) reacting an alkyl-substituted compound of the formula

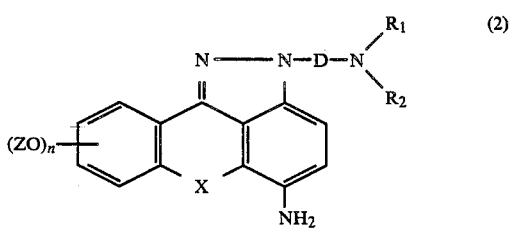

wherein X, $R_1$, $R_2$, and D are as described above, Z is an alkyl of from one to four carbon atoms, and n is an integer of from one to four;

with excess boron tribromide in a suitable organic solvent then with methanol to give a hydroxylated compound of the formula

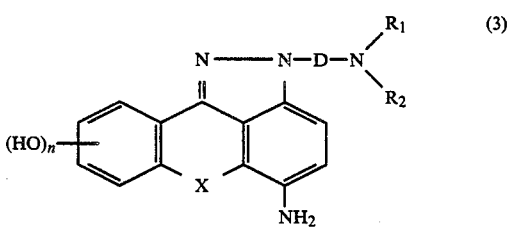

wherein X, n, D, $R_1$, and $R_2$ are as described above;

(b) reacting a compound of Formula 3 with the N-acylimidazole derived from the reaction of 1,1'-carbonyldiimidazole and an N-trityl amino acid such as glycine, an alanine, butyric acid, in N,N-dimethylformamide to give a salt of the corresponding trityl-protected amino acid compound of formula

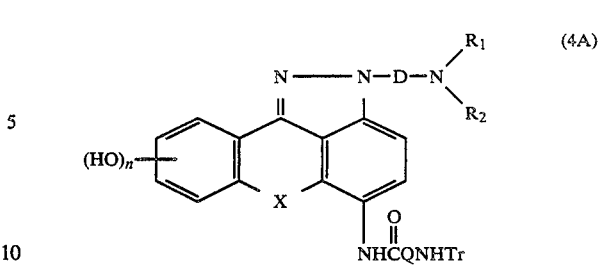

wherein X, $R_1$, $R_2$, D, and n are as described above, Q is a straight or branched alkylene group of from one to four carbon atoms, and Tr is $C(C_6H_5)_3$;

(c) precipitating a salt of a compound of Formula 4A above and recovering a compound of Formula 4A;

(d) reducing the carbonyl portion of a compound of Formula 4A to the corresponding methylene-containing compound of Formula 5A;

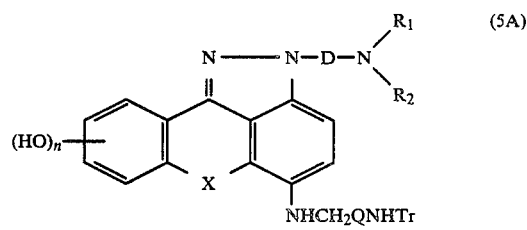

(e) purifying a compound of Formula 5A by recrystallization;

(f) removing the trityl-protecting group from a compound of Formula 5A by reaction with an acid to produce a compound of the instant invention of Formula 1 above.

Preferred compounds of the processes of the present invention are:

5-[(2-aminoethyl)amino]-2-[2-(diethylamino)ethyl]-2H-[1]benzothiopyrano[4,3,2-cd]indazol-8-ol, trihydrochloride, 5-[(2-aminoethyl)amino]-2-[2-(diethylamino)ethyl]-2H-[1]benzothiopyrano[4,3,2-cd]indazol-9-ol, trihydrochloride, N-[2[2-(diethylamino)ethyl]-8-hydroxy-2H-[1]benzothiopyrano[4,3,2-cd]indazol-5-yl-2-[(triphenylmethyl)amino]acetamide, 2-[2-(diethylamino)ethyl]-5-[(2-(triphenylmethyl)aminoethyl]amino-2H-[1]benzothiopyrano[4,3,2-cd]indazol-8-ol, N-[2[2-(diethylamino)ethyl]-9-hydroxy-2H-[1]benzothiopyrano[4,3,2-cd]-indazol-5-yl-2-[(triphenylmethyl)amino]acetamide, and 2-[2-(diethylamino)ethyl]-5-[(2-(triphenylmethyl)aminoethyl]amino-2H-[1]benzothiopyrano[4,3,2-cd]indazol-9-ol.

DETAILED DESCRIPTION

For purposes of illustration the following schematic diagrams show alternative preparative procedures. Steps A, B, and C illustrate a process wherein a primary amine, Compound 1, is alkylated as in U.S. Pat. No. 4,604,390.

This sequence involves harsher conditions and a lower yield and purity of the final product than the process of the instant invention. Steps D, E, and F illustrate a process whereby compound is acylated and then the two protecting groups are removed simultaneously as known in the art. This process does not provide the same purity as the process of the present invention. Steps G, H, I, and J are illustrative of one process of the present invention. Steps K, L, M, N, and O are illustrative for another process of the present invention which involves a recrystallization step which provides a highly pure product. This process is especially suitable for large-scale production as it is efficient and economical. The use of the trityl group provides stable, crystalline, and high melting intermediates which may be purified by recrystallization from organic solvents (Steps (4) and (5)) which is suitable for large-scale production.

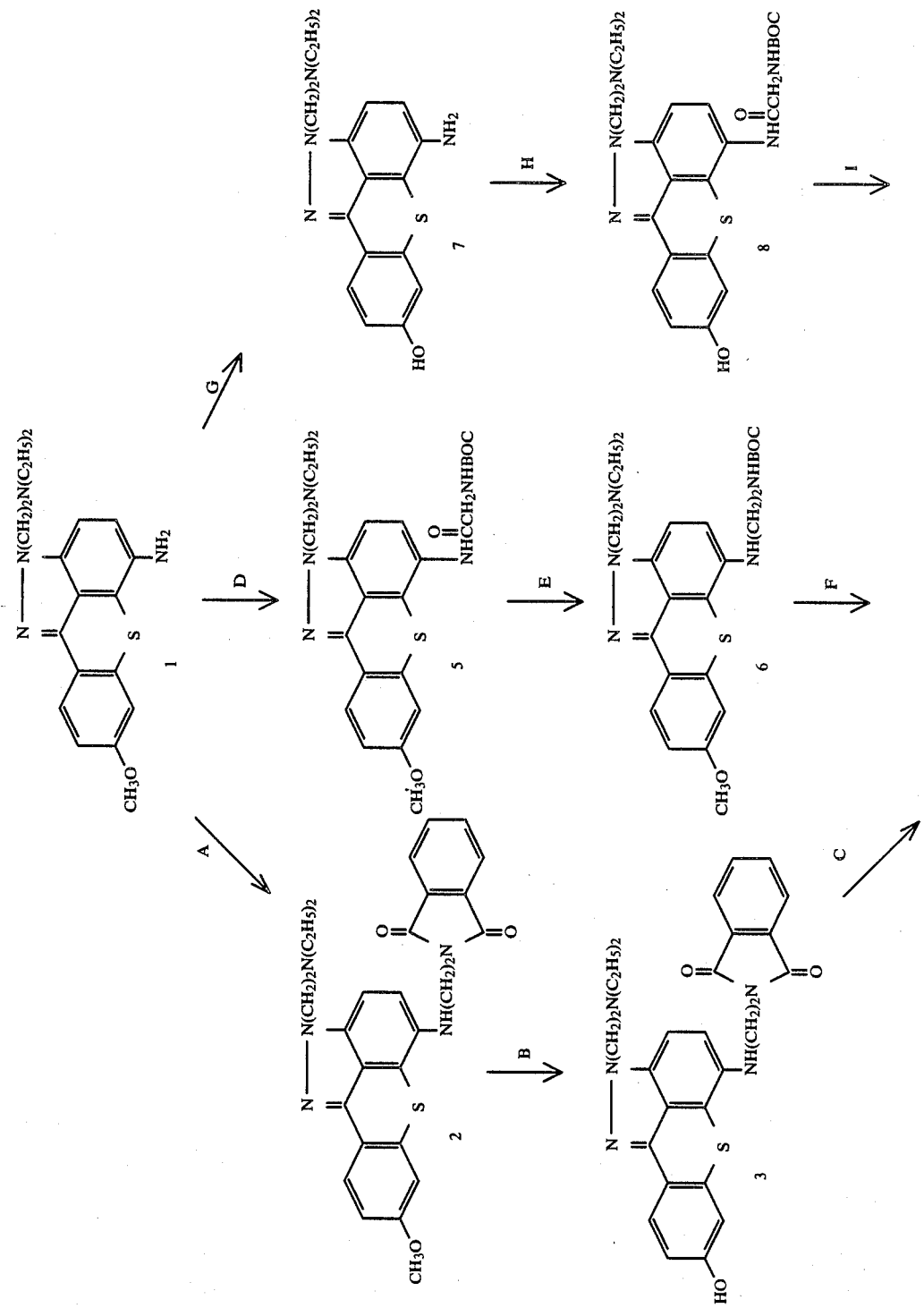
Scheme I

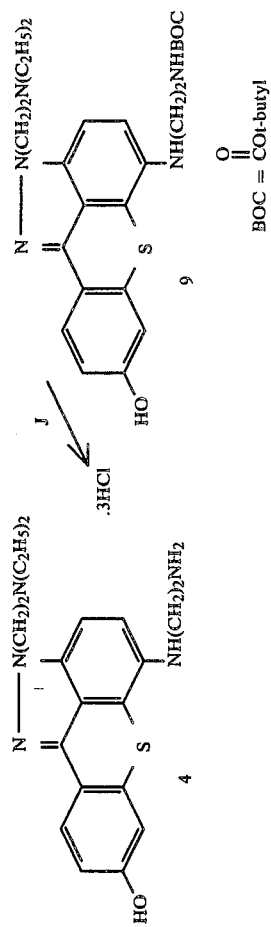

Schematic Step G involves the removal of the methoxy protecting group from compound 1

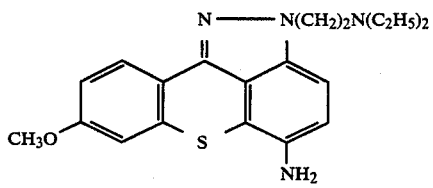

This removal occurs by reaction of Compound 1 with excess boron tribromide in a suitable solvent. The excess is at least one molar excess. Then the compound is reacted with methanol to break up the boron complex to form the corresponding hydroxy-substituted compound

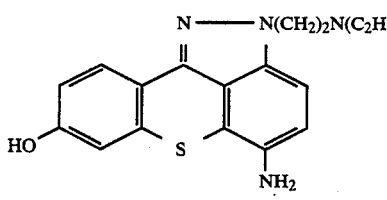 (7)

The reaction between boron tribromide in a suitable solvent and Compound 1 occurs in any of a variety of reaction-inert solvents such as 1,2-dichloroethane, chloroform, or dichloromethane. The preferred inert solvent is 1,2-dichloroethane. The reaction works best with about a 6:1 molar ratio of boron tribromide to Compound 1.

The reaction mixture is heated to from 40° to 55° C. for from 12 to 20 hours. Preferably the mixture is heated to about 45° to 50° C. for about 15 to 18 hours. An excess of methanol is added to the above mixture and the resulting mixture is refluxed for from three to eight hours. Preferably refluxing is carried out for about 5½ hours. The compound is recovered as a hydrobromide salt of Compound 7. Preferably the alkoxy substituted compound is 5-amino-N,N-diethyl-8-methoxy-2H[1]-benzo(chalcogeno)[4,3,2-cd]indazole-2-ethanamine.

In schematic Step H the primary amine of Compound 7 is converted into the corresponding BOC-protected amide, Compound 8. A solution of the N-acylimidazole derived from the reaction of 1,1'-carbonyldiimidazole with [(1,1-dimethylethoxy)carbonyl]glycine in N,N-dimethylacetamide, is treated with the hydrogen bromide salt of Compound 7 to form Compound 8. The reaction between the diimidazole and the glycine is in 1:1 molar ratio in an inert solvent such as in N,N-dimethyformamide or N,N-dimethylacetamide at about room temperature in about one-half hour. Then Compound 7 is added to the above mixture and the subsequent reaction proceeds at about room temperature for from 15 to 25 hours. Preferably the reaction proceeds for from 20-22 hours.

In Schematic Step I the carbonyl group of Compound 8 is reduced to the corresponding methylene group of Compound 10. Compound 9 is reduced by reaction with sodium bis(2-methoxyethoxy)aluminum hydride in toluene at from 60° to 90° C. Preferably at about 70° to 85° C. Compound 10 is isolated by flash chromatography on a silica gel column. The subsequent elution is done with about a 9:1 dichloromethane:methanol solution.

In schematic Step J the BOC-protecting group of Compound 9 is converted into the corresponding Compound 4 with a free amino terminus. Compound 9 is dissolved in a polar inert solvent such as methanol or ethanol. Preferably absolute ethanol is used. This mixture is cooled to about ice temperature and treated with anhydrous hydrogen chloride repeatedly. Compounds of Formula 1 are produced. Preferably the compound 5-[(2-aminoethyl)amino]-2-[2-(diethylamino)ethyl]-2H-benzothiopyrano[4,3,2-cd]indazol-8-ol, trihydrochloride.

Scheme II

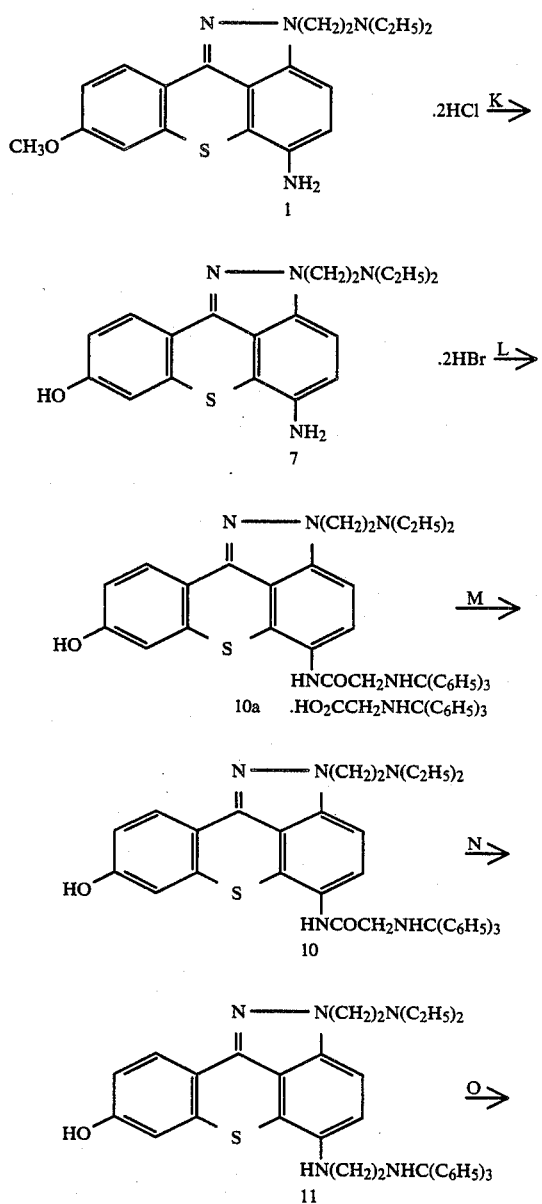

Scheme II -continued

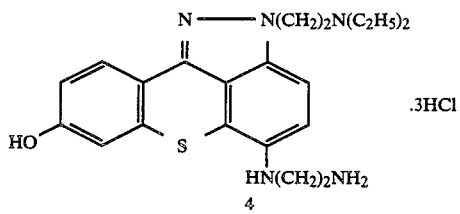

In Scheme II above, schematic Step K, as in schematic Step G of Scheme I, involves the removal of the methoxy protecting group from compound

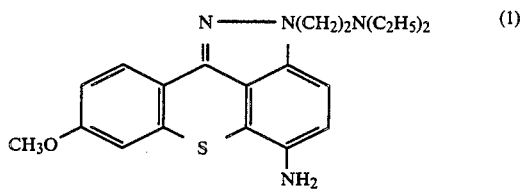

This removal occurs by reaction of Compound 1 with excess boron tribromide in a suitable solvent. The excess is at least one molar excess. Then the compound is reacted with methanol to break up the boron complex to form the corresponding hydroxy-substituted compound

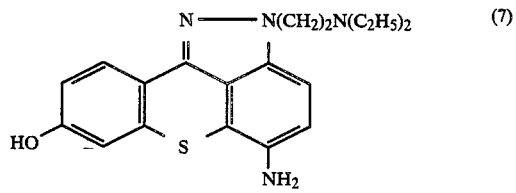

The reaction between boron tribromide in a suitable solvent and Compound 1 occurs in any of a variety of reaction-inert solvents such as 1,2-dichloroethane, chloroform, or dichloromethane. The preferred inert solvent is dichloromethane and 1,2-dichloroethane in a ratio of about 1:1. The reaction works best with about a 3:1 to 5:1 molar ratio of boron tribromide to Compound 1.

The reaction mixture is heated from about 40° to above 85° C. for from 12 to 20 hours. Preferably the mixture is heated to about 50° to 65° C. for about 15 to 18 hours. An excess of methanol is added to the above mixture and the resulting mixture is refluxed for from three to eight hours. Preferably the refluxing is carried out for about 4 to 5½ hours. The compound is recovered as a hydrobromide salt of Compound 7. Preferably the alkoxy-substituted compound is 5-amino-N,N-diethyl-8-methoxy-2H[1]-benzo(chalcogeno)[4,3,2-cd]indazole-2-ethanamine.

In schematic Steps L and M, the primary amine of Compound 10 is converted into the corresponding trityl-protected amide, Compound 10. A solution of the N-acylimidazole derived from the reaction of 1,1'-carbonyldiimidazole in N,N-dimethylformamide and N-trityl-glycine is reacted with Compound 7 to form Compound 10a. The reaction between the diimidazole and the N-trityl-glycine is in about a 1:1 molar ratio at about room temperature for about two hours. Then Compound 7 is added to the mixture and the subsequent reaction proceeds at room temperature for from 16-24 hours. Preferably the ratio of N-acylimidazole to the amino group is 1:2. Preferably it proceeds for about 18 hours. The product, 10a, is treated with an excess of at least two and preferably five to ten molar excess of triethylamine in methanol and ethylacetate mixture in a ratio of about 6:1 to produce Compound 10.

In Schematic Step N the carbonyl group of Compound 10 is reduced to the corresponding methylene group of Compound 11. Compound 10 is reduced by reaction with lithium aluminum hydride or sodium bis(2-methoxyethoxy)-aluminum hydride in a suitable organic solvent. Preferably the reduction is performed with sodium bis(2-methoxyethoxy)-aluminum hydride in toluene at from about 60° to 90° C.; preferably at about 65° to 75° C. The above reaction mixture is carefully treated with water and, extracted with ethyl acetate and then with ethyl acetate: tetrahydrofuran as a 1:1 mixture.

The product, Compound 11, is purified by recrystallization. Compound 11 is placed in an organic solvent such as methanol, acetonitrile, dichloromethane, or ethyl acetate; preferably methanol, acetonitrile, and ethyl acetate are used in a ratio of about 1:1:2.

In schematic Step O the trityl protecting group of Compound 11A is converted into the corresponding Compound 4A with a free amino terminus. Compound 11A is mixed with an inert solvent such as dichloromethane and dissolved when 2,2,2-trifluoroethanol is added. Hydrochloric acid is added; preferably concentrated hydrochloric acid is used. Compounds of Formula 1 are produced.

Scheme III

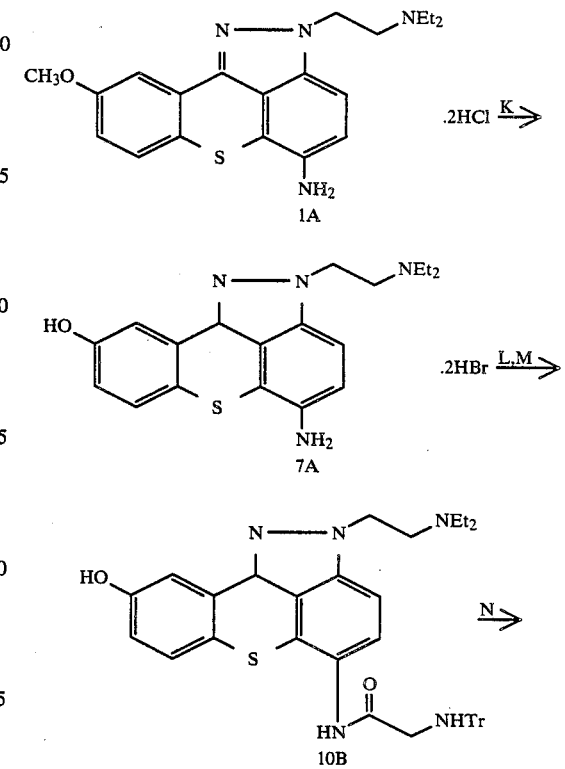

-continued
Scheme III

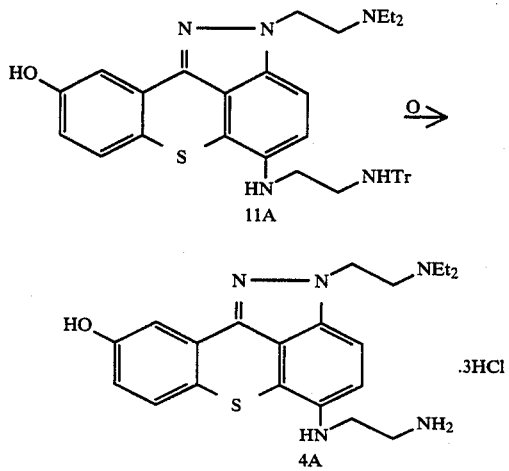

Scheme III above provided proceeds as in Scheme II above and provides a compound named 5-[(2-aminoethyl)amino]-2-[2(diethylamino)ethyl]-2H-[1]benzothiopyrano[4,3,2-cd]indazol-9-ol, trihydrochloride. Preferably the compound is 5-[(2-aminoethyl)amino]-2-[2-(diethylamino)ethyl]-2H-benzothiopyrano[4,3,2-cd]indazol-8-ol, trihydrochloride or 5-[(2-aminoethyl)amino]-2-[2(diethylamino)ethyl]-2H-benzothropyrano[4,3,2-cd]indazole-9-ol, trihydrochloride.

Examples 1, 2, and 3 illustrate the process in Steps A, B, and C.

Examples 4, 5, and 6 illustrate the process in Steps D, E, and F.

Examples 7-19 are meant to be illustrative of the present invention. These examples are presented to exemplify the invention and are not to be construed as limiting the scope of the invention.

EXAMPLE 1

2-[2-[[2-[2-(Diethylamino)ethyl]-8-methoxy-2H-[1]benzothiopyrano[4,3,2-cd]indazol-5-yl]amino]ethyl]-1H-isoindole-1,3(2H)-dione (2)

A solution of 441.4 g (1.0 mol) of 5-amino-N,N-diethyl-8-methoxy-2H-[1]benzothiopyrano[4,3,2-cd]indazole-2-ethanamine, dihydrochloride (1, U.S. Pat. No. 4,604,390) in 8.9 L of water was adjusted to pH 10 with 2.5 L of 2N aqueous sodium hydroxide. The precipitated free base was extracted into 52 L of dichloromethane. The organic phase was washed with water and concentrated to a residual solid that was dried by azeotropic distillation with 7.4 L of toluene then ground in a mortar to a fine powder. This was thoroughly mixed with 393.8 g (1.55 mol) of N-(2-bromoethyl)phthalimide and 109.2 g (1.3 mol) of sodium bicarbonate. The mixture was stirred at 100°-106° C. for 19 hr, then cooled to 25° C. The hardened solid mass was digested in a mixture of dichloromethane and water. The organic phase was washed with water, dried, and concentrated to a gummy residue that was triturated in diethyl ether. The solids were collected by filtration to give 545.5 g of crude product that was dissolved in 40 L of acetonitrile. The solution was clarified with charcoal then maintained at 0°-5° C. overnight. The precipitated solids were collected by filtration, washed with cold acetonitrile, and dried at 220 mm/37° C./1.25 hr to give 324.1 g (59.8%) of pure 2, l mp 171°-172.5° C., 99.1% pure by HPLC.

EXAMPLE 2

2-[2-[[2-[2-(Diethylamino)ethyl]-8-hydroxy-2H-[1]benzothiopyrano[4,3,2-cd]indazol-5-yl]amino]ethyl]-1H-isoindole-1,3(2H)-dione, dihydrobromide (3)

A 25° C. solution of 324.1 g (0.598 mol) of 2-[2-[[2-[2-(diethylamino)ethyl]-8-methoxy-2H-[1]benzothiopyrano[4,3,2-cd]indazol-5-yl]amino]ethyl]-1H-isoindole-1,3(2H)-dione (2) in 7.45 L of dichloromethane was treated dropwise over 2 hr with 2.1 L (2.1 mol) of a 1M solution of boron tribromide in dichloromethane. The mixture was heated at reflux for 6.75 hr, treated with an additional 300 mL (0.3 mol) of boron tribromide solution, then further heated overnight. The refluxing mixture was treated cautiously with 1.86 L of methanol, heated an additional 12 hr, then cooled and stirred for 3 hr in an ice bath. The solids were collected by filtration, washed successively with dichloromethane and hexane, then dried at 220 mm/45° C./20 hr to give 291.8 g (70.8%) of 3, mp 232.5°-234° C., 98.9% pure by HPLC.

EXAMPLE 3

5-[(2-Aminoethyl)amino]-2-[2-(diethylamino)ethyl]-2H-[1]benzothiopyrano[4,3,2-cd]indazol-8-ol, trihydrochloride (4)

A suspension of 5 g (7.25 mmol) of 2-[2-[[2-[2-(diethylamino)ethyl]-8-hydroxy-2H-[1]benzothiopyrano[4,3,2-cd]indazol-5-yl]amino]ethyl]-1H-isoindole-1,3(2H)-dione, dihydrobromide (3) in 150 ml of methanol was treated dropwise with 9.6 mL of anhydrous methylhydrazine and the mixture was stirred at 25° C. for 21 hr. The solution was filtered through Celite® then concentrated to an oily residue which was cooled in an ice bath and treated with 30 mL of 2N hydrochloric acid. The precipitated solids were filtered and the aqueous filtrate was successively heated at 45°-50° C. for 10 minutes, stirred at 25° C. for 10 minutes, and cooled at 5° C. for 30 minutes. Additional precipitated solids were filtered and washed with 25 mL of chilled water. The aqueous filtrate was clarified with charcoal, treated with 1 mL of Dowex 1X2-100 (Cl−) ion exchange resin, and stirred at 5° C. for 50 minutes. The solution was filtered through Celite® and the filtrate was diluted with 1.3 volumes of absolute ethanol. The ice-cold solution was treated portionwise with 0.15 volume of a 10N solution of hydrogen chloride in 2-propanol. After standing overnight at 0°-5° C., the solids were collected by filtration, washed successively with absolute ethanol, ether, then hexane, and dried to give 2.95 g (80%) of 4, mp 261°-263° C. (dec). A 2.6 g sample was dissolved in a mixture of 20 mL of water and 80 mL of absolute ethanol. The ice-cold solution was treated as above with 15 mL of hydrogen chloride in 2-propanol, then maintained at 0°-5° C. for 4 hr. Filtration of the precipitated solids followed by washings as described above and drying at 0.8 mm/50° C./overnight gave 2.35 g (90%) of 4, mp 263°-265° C., 96.5% pure by HPLC.

Overall yield by steps A, B, and C=38.1%

EXAMPLE 4

[2-[[2-[2-(Diethylamino)ethyl]-8-methoxy-2H-[1]benzothiopyrano[4,3,2-cd]indazol-5-yl]amino]-2-oxoethyl]-carbamic acid; 1,1-dimethylethyl ester(5)

A mixture of 44.96 g (0.1 mol) of 5-amino-N,N-diethyl-8-methoxy-2H-[1]benzothiopyrano[4,3,2-cd]indazole-2-ethanamine, dihydrochloride (1), 30.6 g (0.175 mol) of [(1,1-dimethylethoxy)carbonyl]glycine, 44.53 g (0.175 mol) of bis(2-oxo-3-oxazolidinyl)phosphonic chloride, 76 mL (0.436 mol) of N,N-diisopropylethylamine, and 449 mL of dichloromethane was stirred for 24 hr at 25° C. The solution was washed successively with 1N aqueous potassium carbonate and water, dried, and concentrated to a residual solid. Trituration in 2-propanol followed by recrystallization from acetonitrile gave 45.1 g (86%) of 5, mp 130°–132° C. A small portion was purified by flash silica gel chromatography with elution by dichloromethane:methanol (20:1). Pure product fractions were concentrated to a solid which was crystallized from acetonitrile to give pure 5, mp 131°–133° C.

EXAMPLE 5

[2-[[2-[2-(Diethylamino)ethyl]-8-methoxy-2H-[1]benzothiopyrano[4,3,2-cd]indazol-5-yl]amino]ethyl]-carbamic acid; 1,1-dimethylethyl ester (6)

An 80° C. solution of 49.94 g (95 mmol) of [2-[[2-[2-(diethylamino)ethyl]-8-methoxy-2H-[1]benzothiopyrano[4,3,2-cd]indazol-5-yl]amino]-2-oxoethyl]-carbamic acid; 1,1-dimethylethyl ester (5) in 120 mL of toluene was treated dropwise over 2.75 hr with 142.6 mL (475 mmol) of a 3.4M solution of sodium bis(2-methoxyethoxy)aluminum hydride in toluene. Following addition, the solution was ice-cooled and treated cautiously with 20 mL of saturated aqueous ammonium chloride, then 200 mL of water. The mixture was filtered through Celite® and the filtrate was concentrated to an aqueous solution which was extracted with three portions of dichloromethane. The combined extracts were washed with water, dried, and concentrated to a residual solid that was purified by flash silica gel chromatography eluting with dichloromethane:methanol (97:3). Pure product fractions were concentrated to a solid which was crystallized from acetonitrile to give 30.7 g (63%) of 6, mp 133°–134° C., 99.9% pure by HPLC.

EXAMPLE 6

5-[(2-Aminoethyl)amino]-2-[2-(diethylamino)ethyl]-2H-[1]-benzothiopyrano[4,3,2-cd]indazol-8-ol (4)

A 25° C. solution of 0.25 g (0.49 mmol) of [2-[[2-[2-(diethylamino)ethyl]-8-methoxy-2H-[1]benzothiopyrano[4,3,2-cd]indazol-5-yl]amino]ethyl]-carbamic acid; 1,1-dimethylethyl ester (6) in 7.5 mL of dichloroethane was treated dropwise with 2.45 mL (2.45 mmol) of a 1M solution of boron tribromide in dichloromethane. The mixture was stirred at 25° C. for 18 hr, treated cautiously with 3 mL of methanol, then heated at reflux for 6 hr. After cooling to 25° C., the precipitated solids were collected by filtration, washed successively with methanol and dichloromethane, and dried at 200 mm/60° C./overnight to give 0.3 g of 4, 95.2% pure by HPLC. The solids were dissolved in 10.6 mL of ethanol:H$_2$O (4:1) and the solution was treated portionwise with 1.6 mL of a 2.6M solution of hydrogen bromide in 2-propanol. After standing overnight at 0°–5° C., the precipitated solids were collected by filtration, washed, and dried as above to give 0.28 g (90%) of 4 as a salt with 2.9 equivalents of hydrogen bromide, mp 282° C. (dec), 96.1% pure by HPLC.

Overall yield for Steps D–F=48.8%

EXAMPLE 7

5-Amino-2-[2-(diethylamino)ethyl]-2H-[1]benzothiopyrano[4,3,2-cd]indazole-8-ol, dihydrobromide (7)

A 25° C. suspension of 75 g (0:17 mol) of 5-amino-N,N-diethyl-8-methoxy-2H-[1]benzothiopyrano[4,3,2-cd]indazole-2-ethanamine, dihydrochloride (1) in 1.35 L of dichloroethane was treated dropwise with 213 g (0.85 mol) of boron tribromide. The mixture was heated at 78° C. for 16 hr, treated cautiously with 1.5 L of methanol, then heated at reflux for 6 hr. After cooling to 25° C., then chilling at −5° C. overnight, the precipitated solids were collected by filtration, washed with cold methanol, and dried at 2 mm/48° C./24 hr to give 84.3 g (96%) of 7 as a salt with 2.0 equivalents of hydrogen bromide, mp 318° C. (dec), 98.3% pure by HPLC.

EXAMPLE 8

[2-[[2-[2-(Diethylamino)ethyl]-8-hydroxy-2H-[1]benzothiopyrano[4,3,2-cd]indazol-5-yl]amino]-2-oxoethyl]-carbamic acid; 1,1-dimethylethyl ester (8)

A 25° C. mixture of 85.6 g (0.52 mol) of 1,1'-carboxyldiimidazole in 465 mL of N,N-dimethylacetamide was treated portionwise with 87.5 g (0.50 mol) of [(1,1-dimethylethoxy)carbonyl]glycine. The solution was stirred for 0.5 hr then treated with 154.6 g (0.282 mol) of 5-amino-2-[2-(diethylamino)ethyl]-2H-[1]benzothiopyrano[4,3,2-cd]indazol-8-ol (7), as a salt with 2.4 equivalents of hydrogen bromide. The mixture was stirred at 25° C. for 21 hr, concentrated to a viscous oil under vacuum, then diluted with 10% aqueous sodium bicarbonate. The aqueous phase was extracted with three portions of dichloromethane and the combined extracts (1.05 L) were washed with water then diluted with 650 mL of methanol. The solution was stirred at 25° C. for 64 hr then concentrated to a residual solid which was triturated with hot acetonitrile. The solids were collected by filtration, washed with acetonitrile, and air-dried at 25° C./3 days to give 133.1 g (91%) of 8, mp 198° C. (dec), 94.7% pure by HPLC.

EXAMPLE 9

[2-[[2-[2-(Diethylamino)ethyl]-8-hydroxy-2H-[1]benzothiopyrano[4,3,2-cd]indazol-5-yl]amino]ethyl]-carbamic acid; 1,1-dimethylethyl ester (9)

An 80° C. solution of 14.4 mL (48.8 mmol) of a 3.4M solution of sodium bis(2-methoxyethoxy)aluminum hydride in toluene was treated portionwise over 30 min with 5 g (9.8 mmol) of [2-[[2-[2-(diethylamino)ethyl]-8-hydroxy-2H-[1]benzothiopyrano[4,3,2-cd]indazol-5-yl]amino]-2-oxoethyl]-carbamic acid; 1,1-dimethylethyl ester (8). Following addition the solution was cooled to 25° C. and 3 mL of saturated aqueous ammonium chloride was added dropwise. The mixture was stirred for 18 hr, diluted with 35 mL of water, and filtered through silica gel. The filtrate was concentrated to an aqueous phase which was extracted with three portions of dichloromethane. The combined extracts were washed with water, dried, and evaporated to a residual oil which was purified by flash chromatography on silica gel eluting with dichloromethane:methanol (93.7). Pure product fractions were concentrated to leave 3.2 g (64%) of 9 as a foam after vacuum drying, 99.3% pure by HPLC.

EXAMPLE 10

5-[(2-Aminoethyl)amino]-2-[2-(diethylamino)ethyl]-2H-[1]benzothiopyrano[4,3,2-cd]indazol-8-ol, trihydrochloride (4)

To an ice-cold solution of 29.4 g (59.1 mmol) of [2-[[2-[2-(diethylamino)ethyl]-8-hydroxy-2H-[1]benzothiopyrano[4,3,2-cd]indazol-5-yl]amino]ethyl]-carbamic acid; 1,1-dimethylethyl ester and 800 mL of absolute ethyl alcohol was slowly bubbled anhydrous hydrogen chloride until the temperature reached 12° C. The mixture was cooled to 3° C., and the bubbling process was repeated three times, then the mixture was warmed to 25° C. After stirring overnight, the solids were collected by filtration then stirred for 30 minutes at 5° C. with a solution of 250 mL of water and 800 mL of ethyl alcohol. The mixture was diluted with an additional 250 mL of ethyl alcohol and stirred at 5° C. for 5 hr, then at −5° C. for 30 minutes. The solids were collected by filtration, washed successively with diethyl ether then hexane, and dried over phosphorus pentoxide at 2 mm/40° C./2 hr then at 2 mm/25° C./48 hr to give 27.6 g (90.5%) of 4 as the trihydrochloride salt and solvated with 0.5 equivalents of water, mp 260°–264° C. (dec), 99.4% pure by HPLC.

Overall yield for Steps D–J is =50.6%

EXAMPLE 11

5-Amino-N,N-diethyl-8-hydroxy-2H-[1]benzothiopyrano-[4,3,2-cd]indazole-2-ethanamine, dihydrobromide (7)

A 12 l four-necked flask was equipped with a mechanical stirrer, steam bath, nitrogen inlet and outlet, dropping funnel with a rubber septum and a condenser connected with an effective scrubber. The methoxy compound 1 (150 g, 0.34 mol) was suspended in 3 l of dichloromethane:dichloroethane/1:1 mixture. Boron tribromide was transferred into the funnel with a flex-needle under argon and was added dropwise to the stirred slurry. The addition took about 40 minutes and the reaction mixture temperature rose from 20° to 32°. The reaction mixture was heated at reflux on a steam bath overnight. The mixture was cooled down to 30° and checked by TLC. No starting material was determined at this point. Methyl alcohol, 5 l, was carefully added to the reaction mixture. After addition of the second liter of methanol the mixture was heated on a steam bath to 55°–57° and kept at reflux for four hours. Then it was allowed to cool to 25°–30° and chilled with an 2-propanol-ice bath overnight. The cold mixture (−6° C.) was filtered with a candle filter, washed with 1 l of cold methanol, transferred to a Buchner funnel using 1 l of methanol and filtered. The collected precipitate was air dried for 20 minutes, then dried in a vacuum oven (200 mm Hg, 42° C.) overnight. This gave 156.4 g (89.2%) of the product, mp 308°–309° (sharp decomposition, browning >300°), 99.2% pure by HPLC.

EXAMPLE 12

N-[2(2(diethylamino)ethyl]-8-hydroxy-2H-[1]benzothiopyrano[4,3,2-cd]indazol-5-yl-2-[triphenylmethyl)amino]acetamide (10)

A 22 l four-necked flask was equipped with a mechanical stirrer, condenser, and nitrogen inlet and outlet. 1,1'-Carbonyldiimidazole (560 g, 3.45 mol) was placed in the flask and dissolved in 4 l of DMF. N-Trityl-glycine was added portionwise as a solid over 30 minutes. The dark mixture was stirred under nitrogen for two hours. Powdered amine 7 was added to the mixture portionwise over 30 minutes to give a dark brown solution. After 18 hours of stirring under nitrogen at room temperature, the reaction mixture was examined by TLC (SiO$_2$, CH$_2$Cl$_2$:MeOH/4:1) which showed only a trace of the starting material. The solution was concentrated on a vacuum rotary evaporator to give a dark oil. The hot oil was poured into 16 l of water with vigorous stirring to furnish a cream solid which was collected by filtration, washed with water as much as needed and dried for 20 hours at 40°/12 mm Hg under a stream of nitrogen to give 4.5 kg of the crude wet product 10a. The solid was placed in a 72 l flask fitted with a stirrer, condenser, nitrogen inlet and outlet and steam bath, and treated with a total of 48 l of methanol, 8 l of ethyl acetate and 1 kg of triethylamine at about 78° for three hours. The reaction mixture was cooled to −1° with a 2-propanol/ice bath and filtered with a candle filter overnight. The precipitate was washed in the flask with 2×8 l of fresh methanol. The solid was collected on a sintered glass funnel, washed with methanol (4×250 ml), dried at 40°/12 mm Hg under nitrogen overnight. This furnished 744 g (73%) of the product, compound 10. mp 214°–216°, 99.6% pure by HPLC.

EXAMPLE 13

2-[2-(diethylamino)ethyl]-5-[(2-(triphenylmethyl)aminoethyl]amino-2H-[1]benzothiopyrano[4,3,2-cd]indazol-8-ol (11)

A 22 l four-necked flask was equipped with a condenser, mechanical stirrer, nitrogen inlet and outlet, thermometer with Therm-o-Watch controller, heating mantel. The flask was charged with 7 l of toluene and 560 ml of sodium bis(2-methoxyethoxy)aluminum hydride in toluene solution and the mixture was heated to 70° under nitrogen. The solid amide, compound 10 (350 g, 0.535 mol) was added portionwise. The dark-red mixture was stirred at 80° for 4.5 hours then allowed to cool down to the room temperature overnight. TLC showed absence of the starting material. The reaction mixture was carefully treated with water. The first part of water, about 25 ml, resulted in a vigorous reaction. Then a total of 3.5 l of water was added and the mixture was transferred into a 30 l beaker and the organic layer was separated. The residual mixture was extracted with ethyl acetate and then with ethyl acetate:tetrahydrofuran/1:1 mixture. Organic layers were separated in a 6 l separating funnel and washed with water (1 l per funnel, to neutral pH). The combined organic layers (62 l total) were dried over Na$_2$SO$_4$ (200 g per 10 l) overnight. The filtered solution was stripped down and azeotropically dried with 5 l of toluene. To the almost dry solid residue, 6 l of methanol was added and the mixture was refluxed in the rotary evaporator at atmospheric pressure for 45 minutes. The flask was removed and left in a cold room overnight. The solid was collected by filtration, washed with 2×0.5 l of cold methanol and dried in a vacuum oven at 40°/10 mm Hg overnight. This gave 316.7 g (92.5%) of product, compound 11, mp 175.5°–178°, which was 98.3% pure by HPLC. A 20-g sample of this material was recrystallized from methanol:acetonitrile:ethyl acetate/250:250:300 ml to give two crops of the product: 16.26 g (81.3%), mp 203°-205°, 99.18% pure by HPLC and 2.9 g (14.5%), mp 201°-203°, 98.52% pure by HPLC.

Both crops after drying overnight in a vacuum oven (200 mm, 45°, 15 hours) contained some acetonitrile as a residual solvent. This was clearly indicated by $^1$H-NMR and microanalysis. After additional drying for 15 hours at 1.5 mm Hg/45° both samples gave satisfactory analytical data and were free of acetonitrile.

EXAMPLE 14

Recrystallization of bulk material

A 72 l five-necked round bottom flask was equipped with condenser, mechanical stirrer, thermocouple, nitrogen inlet and outlet, and steam bath. The crude compound 11 was placed in the flask under nitrogen, mixed with methanol and acetonitrile (14.5 l each), and the mixture was heated to 61° C. Ethyl acetate, 24 l, was added and the mixture was heated at reflux for one hour. The hot solution was filtered into three 20 l carboys which were cooled overnight at 2° C. The highly crystalline precipitate was collected by filtration in a 3 l fritted glass funnel, washed with cold methanol (3×0.25 l) and dried in a Buflovac ® oven at 35°/12 mm Hg for 15 hours. The insoluble material left in the 72 l flask was dissolved in methanol:acetonitrile:ethyl acetate/2:1:4 l mixture at reflux for 30 minutes. When filtered and cooled as above, it gave the second portion of the material (81 g). The mother liquors gave after additional cooling two more crops. The above lots were dried, analyzed, blended, and screened through a Number 20 sieve to give 1013 g of the penultimate 11. mp 198°-200°, 99.2% pure by HPLC.

EXAMPLE 15

5-[(2-Aminoethyl)amino]-2-[2-(diethylamino)ethyl]-2H-[1]benzothiopyrano[4,3,2-cd]indazol-8-ol, trihydrochloride (4)

A 2 l four-necked flask was equipped with a stirrer, an argon blanket adapter, a thermometer, and an addition funnel. The penultimate (11) (12.8 g, 0.02 mol) was mixed under argon with 200 ml of dichloromethane and dissolved when 100 ml of 2,2,2-trifluoroethanol was added. Ascorbic acid (0.21 g) was added to the solution followed by dropwise addition of 57 ml of ~9N HCl. A yellow-green slurry gradually formed and, after five minutes of stirring, 200 ml of water was added. The two-phase mixture was stirred for additional ten minutes and a TLC sample was taken. More solid appeared and an additional amount of water (2×150 ml) was added to dissolve it. Stirring was continued for ten more minutes. Total reaction time was 45 minutes. The reaction mixture was transferred into a 1 l separating funnel equipped with an inert gas inlet-outlet adapter and the layers were separated. The water layer was washed with dichloromethane (3×100 ml). Total volume of the water layer was about 650 ml and it was diluted with 2600 ml of ethanol. The second portion of ascorbic acid, 0.21 g, was added followed by 42 ml of about 9N HCl/2-propanol solution. The mixture was flushed with argon, sealed and left in a cold room for 1.5 hours. Then another portion, 5 ml, of HCl/2-propanol solution was added and a precipitate started to form. The sealed mixture was left in the cold room for seven hours. The precipitate was collected by filtration under argon and washed with 150 ml of hexane. The wet creamish solid was dissolved in 75 ml of water, 0.11 g of ascorbic acid was added, and the solution was mixed with 300 ml of ethanol followed by 15 ml of the HCl/2-propanol solution. The precipitate formed immediately and the mixture was left under argon in the cold room for ten hours. The very thick mixture was filtered and the precipitate was washed with hexane, dried in a vacuum oven, without bleed, (1 mm Hg, room temperature, P$_2$O$_5$) for 20 hours. This gave 8.85 g (86.5%) of off-white fluffy solid, dec. >260°, 99.4% pure by HPLC.

Overall yields for Steps K→O are from 50 to 55%.

EXAMPLE 16

5-Amino-2-[2-(diethylamino)ethyl]-2H-[1]benzopyrano[4,3,2-cd]indazol-9-ol, dihydrobromide (7A)

A solution of 98 g (0.222 mol) of 5-amino-N,N-diethyl-9-methoxy-2H-[1]benzothiopyrano[4,3,2-cd]indazole-2-ethanamine dihydrochloride (Compound 1A), in 900 ml 1,2-dichloroethane, was treated with 444 ml of a 1M solution of boron tribromide in dichloromethane (0.444 mol). The mixture was heated to 50° C. for 24 hours at which time 200 ml of the boron tribromide solution (0.200 mol) were added, and the reaction maintained at 50° for an additional 24 hours. The mixture was cooled, and methanol (600 ml) was carefully added. The mixture was heated under reflux for three hours, then cooled at 0° for 48 hours. The yellow precipitate was collected by suction filtration, washed with cold methanol, then dried at 60°, 200 mm Hg, affording 110.4 g of 5-amino-2-[2-(diethylamino)ethyl]-2H-[1]benzothiopyrano[4,3,2-cd]indazol-9-ol, hydrobromide with 1.8 equivalents of hydrogen bromide, mp 305° (decomposition), 98.36% pure by HPLC.

EXAMPLE 17

N-[2(2(Diethylamino)ethyl]-9-hydroxy-2H-[1]benzothiopyrano[4,3,2-cd]indazol-5-yl-2-[(triphenylmethyl)amino]acetamide (10B)

A solution of 29.52 g (0.182 mol) of carbonyldiimidazole in 375 ml anhydrous DMF, was treated with 61.1 g (0.193 mol) of trityl glycine, portionwise, over the period of an hour. The mixture was stirred for 45 minutes, at which time 47 g (0.091 mol) of 5-amino-2-[2-(diethylamino)ethyl]-2H-[1]benzothiopyrano[4,3,2-cd]indazol-9-ol, hydrobromide (Compound 7A) was added. This mixture was stirred for 48 hours, then the DMF was evaporated at reduced pressure affording a viscous dark oil which was treated with 600 ml H$_2$O, and the resulting tan solid was collected by suction filtration, and washed with H$_2$O. This solid was suspended in a mixture of 750 ml of methanol and 50 ml of triethylamine, and heated under reflux for two hours. The reaction was placed in the cold for 48 hours then filtered to give the product as a tan solid 48.55 g (80%), mp 239-240.5, 94.58% pure by HPLC.

EXAMPLE 18

2-[2-(Diethylamino)ethyl]-5-[(2-(triphenylmethyl)aminoethyl]amino-2H-[1]benzothiopyrano[4,3,2-cd]indazol-9-ol (11A)

To an 80° C. solution consisting of 94.6 ml of a 3.4M solution of sodium bis(2-methoxyethoxy)aluminum hydride in toluene (0.325 mol) and 86 ml of toluene was added 43.0 g (0.065 mol) N-[2-[2-(diethylamino)ethyl]-9-hydroxy-2H-[1]benzothiopyrano[4,3,2-cd]indazol-5-yl]-2-[(triphenylmethyl)amino]acetamide (Compound 10B) portionwise over a 45-minute period. The reaction was maintained at 80° C. for 2.5 hours, then cooled to 25° C. and stirred an additional 18 hours, then quenched with 47 ml of H₂O. THe solid which formed was placed in a sintered glass funnel, and extracted ten times with a total of 4500 ml of chloroform. The combined extracts were evaporated to dryness then redissolved in 310 ml hot ethyl acetate, and the insolubles filtered. The filtrate was again evaporated to dryness, and the residue heated under reflux in methanol (650 ml) for 0.5 hour, then chilled (3°) for 18 hours. Suction filtration followed by oven drying afforded 33.5 g of yellow solid, which was again refluxed in methanol (525 ml), cooled, filtered, and dried affording 31.6 g of yellow solid (76%), mp 137–139, 97.04% pure by HPLC.

EXAMPLE 19

5-[(2-Aminoethyl)amino]-2-[2-(diethylamino)ethyl]-2H-[1]benzothiopyrano-[4,3,2-cd]-indazol-9-ol, trihydrochloride (4A)

A mechanically stirred solution of 31 g (0.048 mol) 2-[2-diethylamino)ethyl]-5-[[2-[(triphenylmethyl)amino]ethyl]amino]-2H[1]benzothiopyrano[4,3,2-cd]indazole-9-ol (Compound 11A), 495 ml dichloromethane, and 247 ml trifluoroethanol, was stirred for ten minutes. A solution of 99 ml concentrated HCl and 99 ml H₂O was added and stirred for ten minutes, at which time an additional 250 ml H₂O was added, and the reaction stirred for 45 minutes. The mixture was transferred to a separatory funnel, layers separated, and the organic layer drained off. The aqueous layer was washed with an additional 200 ml of dichloromethane, then treated with 750 ml ethanol, and 20 ml of 6.22M isopropanolic hydrogen chloride, then cooled for 2.5 hours. The mixture was filtered, and the white solid dissolved in 250 ml H₂O. Ethanol (700 ml), and 5 ml of 6.22M isopropanolic hydrogen chloride, were added, and the mixture cooled (−5°) for 18 hours. The white solid was collected by suction filtration affording 21.02 g product, mp 270° (dec.) 98.91% pure by HPLC.

We claim:

1. A process for the preparation of a substituted benzo(chalcogeno)[4,3,2-cd]indazole of the formula

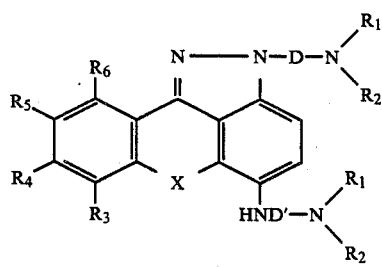

or a pharmaceutically acceptable salt thereof, wherein
X is oxygen, sulfur, or selenium;
D is a straight or branched alkylene group of from two to eight carbon atoms;
D' is ethylene;
$R_1$ and $R_2$ may be the same or different and are hydrogen or an alkyl group of from two to eight carbon atoms which may be substituted by hydroxy; and
$R_3$, $R_4$, $R_5$, and $R_6$ may be the same or different are hydrogen or hydroxy which comprises:
(a) reacting an alkyl-substituted compound of the formula

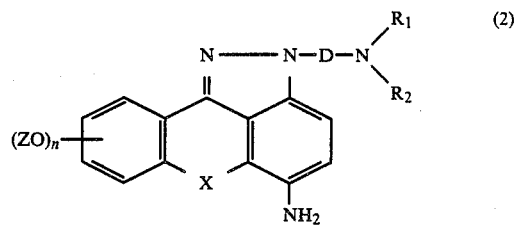

wherein X, $R_1$, $R_2$, and D are as described above, Z is an alkyl of from one to four carbon atoms, and n is an integer of from one to four;
with excess boron tribromide in a suitable organic solvent then with methanol to give a hydroxylated compound of the Formula

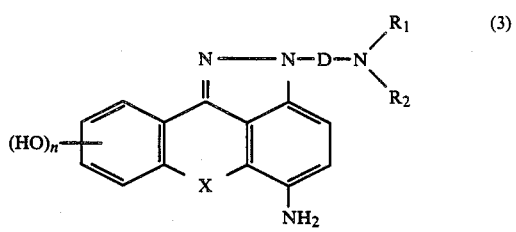

wherein X, n, D, $R_1$, and $R_2$ are as described above;
(b) reacting a compound of Formula 3 with the N-acylimidazole derived from the reaction of 1,1'-carbonyldiimazole and N-trityl glycine, or N-trityl alanine in N,N-dimethylformamide to give a salt of the corresponding trityl-protected amino acid compound of Formula

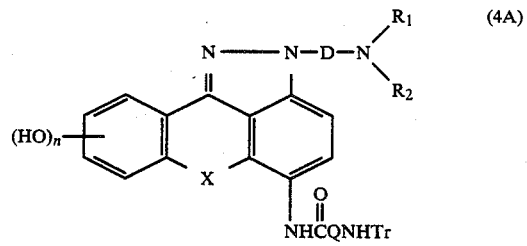

wherein $X_1$, $R_1$, $R_2$, D, and n are as described above, Q is a methylene group, and Tr is $C(C_6H_5)_3$;
(c) precipitating a salt of a compound of Formula 4A above and recovering a compound of Formula 4A;
(d) reducing the carbonyl portion of a compound of Formula 4A to the corresponding methylene-containing compound of Formula 5A

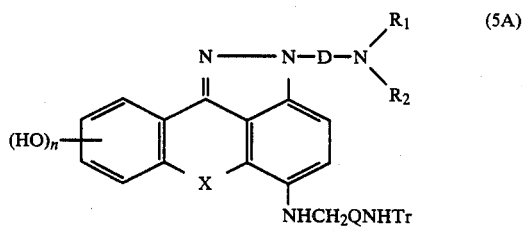

(e) purifying a compound of Formula 5A by recrystallization;
(f) removing the trityl-protecting group from a compound of Formula 5A by reaction with an acid to produce a compound of the instant invention of Formula 1 above.

2. The process of claim 1 wherein in Step (a) the reactants are boron tribromide and methanol.

3. The process of claim 1 wherein in Step (a) the reaction time is from 15 to 20 hours at a temperature of from 50° to 65° C.

4. The process of claim 1 wherein in Step (a) n is 1 and Z is methyl.

5. The process of claim 1 wherein in Step (a) the alkoxy substituted compound is 5-amino-N,N-diethyl-8-methoxy-2H-[1]benzo(chalcogeno)-[4,3,2-cd]indazole-2-ethanamine.

6. The process of claim 1 wherein in Step (a) X is sulfur.

7. The process of claim 1 wherein in Step (a) the organic solvent is a mixture of dichloromethane and 1,2-dichloroethane in a ratio of 1:1.

8. The process of claim 1 wherein in Step (b) the ratio of a compound of Formula 3 to reactants 1,1'-carbonyldiimidazole and N-trityl-glycine is from 1:2:2 to 1:3:3.

9. The process of claim 1 wherein in Step (c) the precipitating agent is water and recovering of compound 4A proceeds by triethylamine in methanol-ethyl acetate mixture.

10. The process of claim 1 wherein in Step (d) the reducing agent is sodium bis(2-methoxyethoxy)aluminum hydride.

11. The process of claim 1 wherein in Step (d) the reduction takes place in toluene and the product is extracted with ethyl acetate and then with an ethyl acetate-tetrahydrofuran mixture in a ratio of 4:1 to 1:1.

12. The process of claim 1 wherein in Step (e) the purifying agent is methanol, acetonitrile, and ethylacetate in a ratio of from 1:1:1 to 1:1:2.

13. The process of claim 1 wherein in Step (f) the reaction mixture is a two-phase mixture of dichloromethane and trifluoroethanol in a ratio of 2:1 and water.

14. The process of claim 1 wherein in Step (f) the reaction time is from 30 minutes to 90 minutes at room temperature.

15. The process of claim 1 wherein in Step (f) the acid is hydrochloric.

16. The process of claim 1 wherein the compound produced is 5-[(2-aminoethyl)amino]-2-[2-(diethylamino)ethyl]-2H-[1]benzothiopyrano[4,3,2-cd]-indazol-8-ol, trihydrochloride.

17. The process of claim 1 wherein the compound produced is 5-[(2-aminoethyl)amino]-2-[2-(diethylamino)ethyl]-2H-[1]benzothipyrano[4,3,2-cd]indazol-9-ol, trihydrochloride.

18. A compound named N-[2[2-(diethylamino)ethyl]8-hydroxy-2H-[1]benzothiopyrano[4,3,2-cd]indazol-5-yl-2-[(triphenylmethyl)amino]acetamide.

19. A compound named 2-[2-(diethylamino)ethyl]-5-[(2-(triphenylmethyl)aminoethyl]amino-2H-[1]benzothiopyrano[4,3,2-cd]indazol-8-ol.

20. A compound named N-[2[2-(diethylamino)ethyl]-9-hydroxy-2H-[1]-benzothiopyrano[4,3,2-cd]indazol-5-yl-2-[(triphenylmethyl)amino]acetamide.

21. A compound named 2-[2-(diethylamino)ethyl]-5-[(2-(triphenylmethyl)aminoethyl]amino-2H-[1]-benzothiopyrano[4,3,2-cd]indazol-9-ol.

* * * * *